United States Patent [19]

Gunkel et al.

[11] Patent Number: 4,766,240

[45] Date of Patent: Aug. 23, 1988

[54] PROCESS FOR PREPARING 2-(ALKYLBENZOYL)BENZOIC ACID

[75] Inventors: Louis T. Gunkel, Yardley, Pa.; John Crosby, Lawrenceville, N.J.

[73] Assignee: FMC Corporation, Philadelphia, Pa.

[21] Appl. No.: 42,072

[22] Filed: Apr. 24, 1987

[51] Int. Cl.$^4$ .............................................. C07C 59/76
[52] U.S. Cl. .................................................. 562/460
[58] Field of Search ....................................... 562/460

[56] References Cited

U.S. PATENT DOCUMENTS

| | | | |
|---|---|---|---|
| 1,547,280 | 7/1925 | Wollaston | 562/460 |
| 3,764,664 | 10/1973 | Suda et al. | 423/495 |
| 4,087,458 | 5/1978 | Emori et al. | 260/517 |

FOREIGN PATENT DOCUMENTS 1243043  10/1986  Japan .................... 562/460

OTHER PUBLICATIONS

Groggins et al., "Studies in the Friedel-Crafts Reactions Naphthalene Series, I–Preparation of Naphthanthraquinone", Ind. & Eng. Chem. 22, Feb. 1930, pp. 157–159.

*Primary Examiner*—Paul J. Killos
*Attorney, Agent, or Firm*—Richard E. Elden; Robert L. Andersen; Eugene G. Seems

[57] ABSTRACT

An environmentally acceptable process is provided to synthesize a 2-(alkylbenzoyl)benzoic acid suitable for synthesizing a 2-alkylanthraquinone without further purification. Usually the crude product is isolated from the reaction mixture by a succession of steps which generate a large volume of aqueous waste. The present process eliminates or decreases these wastes and produces a product of sufficient purity for synthesizing as 2-alkylanthraquinone.

8 Claims, No Drawings

PROCESS FOR PREPARING 2-(ALKYLBENZOYL)BENZOIC ACID

The present invention is a process for preparing a 2-(alkylbenzoyl)benzoic acid in a form suitable for synthesizing a 2-alkylanthraquinone while decreasing discharges of aqueous wastes to the environment during the work-up steps.

It is well known that 2-(alkylbenzoyl)benzoic acids are useful to synthesize the substituted anthraquinones which are employed to manufacture hydrogen peroxide. As alkylanthraquinones are expensive it is desirable to provide a simple, less expensive, and more environmentally acceptable method of preparing a pure (alkylbenzoyl)benzoic acid from the reaction of phthalic anhydride and an alkylbenzene.

Normally, the crude product is "worked-up" to recover the pure product. That is, the reaction mixture is quenched in dilute sulfuric acid, and the organic phase is separated, washed several times with water and then extracted with dilute caustic. The caustic solution is then acidified to deposit the product acid which is then filtered, washed thoroughly with water and dried. Alternatively, the product may be recovered by steam distillation. The product formed usually consists of tan to brown nodules which requires recrystallization to yield a product sufficiently pure to synthesize the corresponding anthraquinone. U.S. Pat. No. 3,764,664 to Suda et al. teaches that this work-up procedure is time consuming and the final crystallization can be eliminated by first preparing fresh anhydrous aluminum chloride by reacting aluminum metal and anhydrous HCl in a trihalobenzene solvent. However, trihalobenzene solvents are well known health hazards, thus undesirable. Further, their relatively high melting points restrict the reaction temperatures which may be employed.

U.S. Pat. No. 4,087,458 to Fumitoshi et al. discloses that the isomerization of alkyl substituents is undesirable. This suggests that it is desirable to avoid operating at elevated temperatures required when either 1,3,5-trichlorobenzene (63° C.) or 1,3,5-tribromobenzene (120° C.) is employed as a solvent. The patent to Suda et al. teaches that isomerization can be suppressed by removing HCl formed during the aluminum chloride catalyzed reaction of phthalic anhydride and alkylbenzene. The patent examples employ the "normal work-up" procedure which generates large volumes of aqueous wastes.

The present invention is a process for synthesizing a 2-(alkylbenzoyl)benzoic acid without generating a large quantity of aqueous waste comprising incorporating phthalic anhydride, an alkylbenzene and aluminum chloride into an inert solvent thereby forming a reaction mixture, maintaining the temperature of the reaction mixture between 0° and 90° C. for a sufficient time to react at least part of the phthalic anhydride and alkylbenzene to form a 2-(alkylbenzoyl)benzoic acid in the reaction mixture, combining the reaction mixture and an aqueous acid thereby forming an aqueous phase and an organic phase, separating the organic phase and the aqueous phase, combining the organic phase with a solvent quantity of a low boiling aliphatic hydrocarbon solvent to precipitate the 2-(alkylbenzoyl)benzoic acid as a solid phase in the combined solvent-organic phase, and separating the solid phase from the solvent-organic phase. The scope of the invention also includes the steps of working up a crude 2-(alkylbenzoyl)benzoic acid to recover a purer 2-(alkylbenzoyl)benzoic acid from the reaction mixture as evidenced by a decreased melting point range and/or decreased color.

Typically, equal molar quantities of phthalic anhydride and benzene or an alkyl benzene are reacted for several hours in the presence of a suitable solvent such as chlorobenzene or orthodichlorobenzene along with aluminum chloride as catalyst. Temperatures of 15° C. to 60° C. are preferred. Subsequently the reaction mixture is "quenched" (transferred into dilute sulfuric acid) in order to decompose the reaction product.

Any alkylbenzene may be employed in practicing the invention, desirably the alkyl group of the alkylbenzene contains from 1 to 5 carbon atoms. Preferably the alkylbenzene is ethylbenzene, t-butylbenzene or t-amylbenzene.

The large volumes of aqueous wastes required by the normal work-up steps of the prior art are eliminated or decreased if, following the quenching acid treatment of the reaction mixture, the organic phase is combined with an aliphatic hydrocarbon solvent. The 2-(alkylbenzoyl)benzoic acid is sufficiently pure when separated to be used without the recrystallization step also required by the prior art "normal work-up".

The process of the present invention is clearly superior to the prior art processes in that it eliminates a series of time-consuming work-up steps, such as, a caustic washing step, an acidification step and water washing of the product. In addition, each of these steps generate aqueous wastes which require disposal. The present process has the advantage of decreasing these aqueous wastes while recovering a purer product as indicated by a decreased melting point range and/or decreased color. Further the present process yields a high quality product without crystallization and the aliphatic hydrocarbon solvent employed in the process can be recycled to further minimize waste disposal problems.

Any low boiling aliphatic hydrocarbon (also known as an alkane or paraffin) may be employed as a solvent, such as butane, heptane, decane, hexane or the like. Suitable petroleum based solvents include commonly available distillate fractions such as petroleum ether, ligroin, naptha and the like. It is desirable for the boiling point of the aliphatic hydrocarbon to be above 30° C. to avoid the need for refrigeration or for pressurized reactors. It is also desirable for the solvent to be a low boiling aliphatic hydrocarbon with a boiling point below 200° C. to minimize the energy employed to evaporate the aliphatic hydrocarbon from the product. An aliphatic hydrocarbon with a boiling point between 35° C. and 125° C. is a preferred solvent. The solvent is desirably recovered from the solvent-organic phase by distillation and may be recycled in the process. Petroleum ether is particularly preferred because of its low cost and ready availability.

The best mode for practicing the process of the invention will be clear to one skilled in the art from the following nonlimiting examples.

COMPARATIVE EXAMPLE

A reaction mixture was prepared by incorporating
200 grams o-dichlorobenzene,
25 grams phthalic anhydride, and
25 grams t-amyl benzene
into a 500 ml four necked flask equipped with stirrer, reflux condenser and thermometer. The mixture was stirred and the flask was purged with nitrogen. Fifty grams of anhydrous aluminum chloride was then added at ambient temperature. A slight exotherm was noted. The reaction mixture was then heated to 48° C. for four hours. The run was followed by observing the disappearance of phthalic anhydride using a gas chromatographic analysis.

The reaction mixture was quenched in 600 ml of 5% $H_2SO_4$ and stirred. An organic layer was separated and washed twice with 250 ml portions of 5% NaOH solution. The caustic wash was then acidified with approximately 20 ml of concentrated $H_2SO_4$. An oil formed in the aqueous solution which formed a gummy solid when cooled with ice water. The solids were filtered from the acid solution, washed twice with water and dried. The resulting brown solids weighed 34.7 grams and corresponded to a 70% yield. The melting point of the product was 127° C. to 135° C.

EXAMPLE 1

2(t-amylbenzoyl)benzoic acid

A 500 ml flask was equipped with a thermometer, a nitrogen sparger, a reflux condenser, a stirrer and a heating mantle. The flask was charged with
200 grams chlorobenzene (1.78 moles)
44 grams phthalic anhydride (0.3 moles)
49 grams 95% t-amylbenzene (0.3 moles), and
80 grams aluminum chloride (0.6 moles).
The flask was sparged with nitrogen and maintained at a reduced pressure with a vacuum. The temperature rose from 26° C. to 40° C. The temperature was subsequently maintained at 35° C. with the heating mantle. After 3.5 hours the reactor contents were poured into a 2 liter beaker containing 1000 grams of a 10% $H_2SO_4$ solution. The organic layer was separated and washed with 400 ml of hot water. Eight hundred ml of cold (15° C.) heptane was added to the organic phase causing a white precipitate to drop out. This precipitate was filtered with a Buchner funnel using a medium paper filter. The wet cake weighed 102 grams. This material was dried in a vacuum oven overnight at 80° C. to yield 57 grams (65% yield) of white product. The melting point of the product was 133°–137° C.

EXAMPLE 2

Example 1 was repeated. The product weighed 61.5 g (69% yield). The melting point of the product was 133°–136° C.

EXAMPLE 3

2-(t-amylbenzoyl)benzoic acid

Example 1 was repeated using
400 grams chlorobenzene,
100 grams phthalic anhydride (0.675 moles)
100 grams t-amylbenzene (0.675 moles) and
200 grams aluminum chloride (1.50 moles).
The product was precipitated with 800 ml heptane at room temperature. After drying 140.65 g (70.4% yield) of product was recovered melting at 136°–139° C.

EXAMPLE 4

2(methylbenzoyl)benzoic acid

Twenty-five grams of phthalic anhydride (0.168 moles), 200 grams of orthodichlorobenzene and 50 grams of anhydrous aluminum chloride (0.376 moles) were charged under nitrogen into a 500 ml three necked flask equipped with stirrer, thermometer, and reflux condenser. An equal molar amount of toluene (15.7 grams, 0.168 moles) was added and the temperature rose from 25° C. to 35° C. The mixture was heated to 50° C. and held for one hour at this temperature.

The reaction mixture was then poured into 600 ml of 10% $H_2SO_4$ and stirred. The organic phase was drawn off and washed twice with 250 ml portions of hot water. The organic phase was then poured into 800 ml of cold (10° C. to 15° C.) petroleum ether and stirred for 30 minutes. A white precipitate fell out of the petroleum ether and was filtered, washed with a small quantity of petroleum ether and dried overnight in a vacuum oven.

The weight of the dried product was 31.89 grams (78.35%).

The melting point of the material was 134°–136° C.

EXAMPLE 5

2(ethylbenzoyl)benzoic acid

Twenty-five grams of phthalic anhydride (0.168 moles), 200 grams of orthodichlorobenzene and 50 grams of anhydrous aluminum chloride (0.376 moles) were charged under nitrogen into a 500 ml three necked flask equipped with stirrer, thermometer and reflux condenser. An equal molar amount of ethyl benzene (18.5 grams, 0.168 moles) was added and the temperature rose from 25° C. to 40° C. The mixture was heated to 50° C. and held for one hour at this temperature.

The reaction mixture was then poured into 600 ml of 10% $H_2SO_4$ and stirred. The organic phase was drawn off and washed twice with 250 ml portions of hot water. The organic phase was then poured into 800 ml of cold (10° C. to 15° C.) petroleum ether and stirred for 30 minutes. A white precipitate was filtered, washed with a small quantity of petroleum ether and dried overnight in a vacuum oven.

The weight of the dried product was 30.86 grams (71.8%).

The melting point of the material was 122° C. to 125° C.

EXAMPLE 6

2(propylbenzoyl)benzoic acid

Twenty-five grams of phthalic anhydride (0.168 moles), 200 grams of orthodichlorobenzene and 50 grams of anhydrous aluminum chloride (0.376 moles) were charged under nitrogen to a 500 ml three necked flask equipped with stirrer, thermometer, and reflux condenser. An equal molar amount of propyl benzene (20.4 grams, 0.168 moles) was added and the temperature rose from 25° C. to 37° C. The mixture was heated to 50° C. and held for one hour at this temperature.

The reaction mixture was then poured into 600 ml of 10% $H_2SO_4$ and stirred. The organic phase was drawn off and washed twice with 250 ml portions of hot water. The organic phase was then poured into 800 ml of cold (10° C. to 15° C.) petroleum ether and stirred for 30 minutes. A white precipitate fell out of the petroleum ether and was filtered, washed with a small quantity of petroleum ether and dried overnight in a vacuum oven.

The weight of the dried product was 33.7 grams (74.2%)

The melting point of the material was 117°–118° C.

EXAMPLE 7

2(butylbenzoyl)benzoic acid

Twenty-five grams of phthalic anhydride (0.168 moles), 200 grams of orthodichlorobenzene and 50 grams of anhydrous aluminum chloride (0.376 moles) were charged under nitrogen to a 500 ml three necked flask equipped with stirrer, thermometer, and reflux condenser. An equal molar amount of butyl benzene (22.8 grams, 0.168 moles) was added and the temperature rose from 22° C. to 35° C. The mixture was heated to 50° C. and held for one hour at this temperature.

The reaction mixture was then poured into 600 ml of 10% $H_2SO_4$ and stirred. The organic phase was drawn off and washed twice with 250 ml portions of hot water. The organic phase was then poured into 800 ml of cold (10° C. to 15° C.) petroleum ether and stirred for 30 minutes. A white precipitate fell out of the petroleum ether which was filtered, washed with a small quantity of petroleum ether and dried overnight in a vacuum oven.

The weight of the dried product was 36.0 grams (75.3%).

The melting point of the material was 128° C. to 131° C.

EXAMPLE 8

2(amylbenzoyl)benzoic acid

Twenty-five grams of phthalic anhydride (0.168 moles), 200 grams of orthodichlorobenzene and 50 grams of anhydrous aluminum chloride (0.376 moles) were charged under nitrogen to a 500 ml three necked flask equipped with stirrer, thermometer, and reflux condenser. An equal molar amount of amylbenzene (25.0 grams, 0.168 moles) was added and the temperature rose from 22° C. to 35° C. The mixture was heated to 50° C. and held for one hour at this temperature.

The reaction mixture was then poured into 600 ml of 10% $H_2SO_4$ and stirred. The organic phase was drawn off and washed twice with 250 ml portions of hot water. The organic phase was then poured into 800 ml of cold (10° C. to 15° C.) hexane (practical) and stirred for 30 minutes. A white precipitate fell out of the hexane which was filtered, washed with a small quantity of ether and dried overnight in a vacuum oven.

The weight of the dried product was 32.72 grams (65.44%).

The melting point of the material was 136°–139° C.

We claim:

1. A process for synthesizing a 2-(alkylbenzoyl)benzoic acid without generating a large quantity of aqueous waste comprising incorporating phthalic anhydride, an alkylbenzene and aluminum chloride into an inert solvent thereby forming a reaction mixture, maintaining the temperature of the reaction mixture between 0° C. and 90° C. for a sufficient time to react at least part of the phthalic anhydride and alkylbenzene to form a 2-(alkylbenzoyl)benzoic acid in the reaction mixture, combining the reaction mixture and an aqueous, dilute acid thereby forming an aqueous phase and an organic phase, separating the organic phase and the aqueous phase, combining the organic phase with a solvent quantity of a low boiling aliphatic hydrocarbon solvent to precipitate the (alkylbenzoyl)benzoic acid as a solid phase in the combined solvent-organic phase, and separating the solid phase from the solvent-organic phase.

2. The process of claim 1 wherein the low boiling aliphatic hydrocarbon solvent is petroleum ether.

3. The process of claim 1 wherein the alkyl group of the alkylbenzene contains from 1 to 5 carbon atoms.

4. The process of claim 2 wherein the alkyl group of the alkylbenzene contains from 1 to 5 carbon atoms.

5. A process for decreasing the aqueous wastes generated by recovering an 2-(alkylbenzoyl)benzoic acid from a reaction mixture prepared by incorporating phthalic anhydride, an alkylbenzene and aluminum chloride into an inert solvent thereby forming a reaction mixture, maintaining the temperature of the reaction mixture between 0° C. and 90° C. for a sufficient time to react at least part of the phthalic anhydride and alkylbenzene comprising combining the reaction mixture and an aqueous, dilute acid thereby forming an aqueous phase and an organic phase, separating the organic phase and the aqueous phase, combining the organic phase with a solvent quantity of a low boiling aliphatic hydrocarbon solvent to precipitate the (alkylbenzoyl)benzoic acid as a solid phase in the combined solvent-organic phase, and separating the solid phase from the solvent-organic phase.

6. The process of claim 5 wherein the low boiling aliphatic hydrocarbon solvent is petroleum ether.

7. The process of claim 5 wherein the alkyl group of the alkylbenzene contains from 1 to 5 carbon atoms.

8. The process of claim 6 wherein the alkyl group of the alkylbenzene contains from 1 to 5 carbon atoms.

* * * * *